(12) United States Patent
Tada et al.

(10) Patent No.: US 7,632,958 B2
(45) Date of Patent: Dec. 15, 2009

(54) TITANIUM COMPLEXES, THEIR PRODUCTION METHODS, TITANIUM-CONTAINING THIN FILMS, AND THEIR FORMATION METHODS

(75) Inventors: Ken-ichi Tada, Kanagawa (JP); Koichiro Inaba, Yamaguchi (JP); Taishi Furukawa, Kanagawa (JP); Hirokazu Chiba, Tokyo (JP); Tetsu Yamakawa, Tokyo (JP); Noriaki Oshima, Kanagawa (JP)

(73) Assignees: Tosoh Corporation, Shunan-shi (JP); Sagami Chemical Research Center, Ayase-shi (JP)

( * ) Notice: Subject to any disclaimer, the term of this patent is extended or adjusted under 35 U.S.C. 154(b) by 0 days.

(21) Appl. No.: 12/093,389

(22) PCT Filed: Nov. 1, 2006

(86) PCT No.: PCT/JP2006/321880

§ 371 (c)(1),
(2), (4) Date: Sep. 16, 2008

(87) PCT Pub. No.: WO2007/055140

PCT Pub. Date: May 18, 2007

(65) Prior Publication Data

US 2009/0036697 A1      Feb. 5, 2009

(30) Foreign Application Priority Data

Nov. 11, 2005  (JP) ............................. 2005-326885

(51) Int. Cl.
*C07F 7/28* (2006.01)
*C23C 16/00* (2006.01)
(52) U.S. Cl. ..................................... 556/51; 427/248.1
(58) Field of Classification Search .................. 556/51; 427/248.1
See application file for complete search history.

(56) References Cited

U.S. PATENT DOCUMENTS

| 5,607,722 | A | | 3/1997 | Vaartstra et al. |
| 5,659,057 | A | * | 8/1997 | Vaartstra ....................... 556/51 |
| 5,908,947 | A | * | 6/1999 | Vaartstra ...................... 556/42 |
| 2004/0110983 | A1 | | 6/2004 | Odom |

FOREIGN PATENT DOCUMENTS

| JP | 2004-196618 A | 7/2004 |
| JP | 2006-93551 A | 4/2006 |

OTHER PUBLICATIONS

Heindirk Tom Dieck, et al, "Diazadiene Complexes of Group 4 Metals I. Synthesis of Mono-, Bis- and Tris(Diazadiene) Titanium Complexes and the Structure of Diazadienedichlorotitanium", Inorganica Chimica Acta, 1990, pp. 191-197, vol. 177, No. 2.

Robin J. H. Clark, et al, "The Chemistry of Methyltitanium Trichloride Synthesis, Properties, Infrared Spectra, and Variable Temperature Nuclear Magnetic Resonance Spectra of Adducts of Methyltitanium Trichloride With Symmetrical Bidentate Ligands", Journal of the Chemical Society (Section) A: Inorganic, Physical Theoretical, 1970, pp. 2026-2033, No. 12.

Ju Youn Kim, et al, "Characteristics and Compositional Variation of Tin Films Deposited by Remote Peald on Contact Holes", Journal of the Electrochemical Society, 2005, pp. G29-G34, vol. 152, No. 1.

Extended European Search Report dated Sep. 23, 2008.

* cited by examiner

*Primary Examiner*—Porfirio Nazario Gonzalez
(74) *Attorney, Agent, or Firm*—Sughrue Mion, PLLC

(57) ABSTRACT

Objects of the present invention are to provide a novel titanium complex that has good vaporization characteristics and an excellent thermal stability, and becomes a raw material for forming a titanium-containing thin film by methods such as CVD method or ALD method, its production method, a titanium-containing thin film formed using the same, and its formation method. In the invention, a titanium complex represented by the general formula (1) is produced by reacting a diimine represented by the general formula (2) and metallic lithium, and then reacting a tetrakisamide complex represented by the general formula (3).

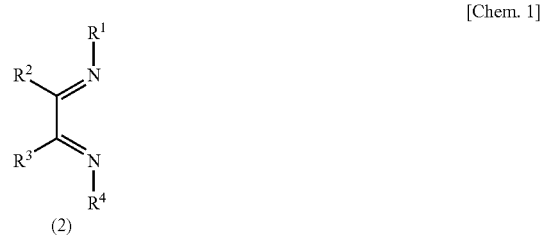

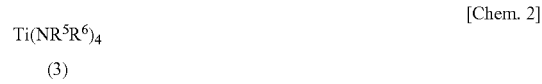

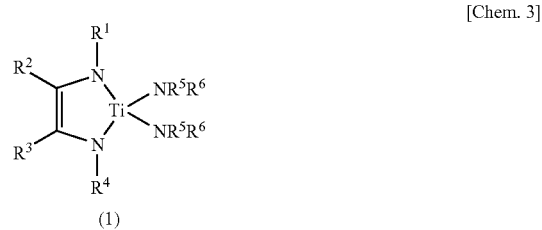

(In the formulae, $R^1$ and $R^4$ represent an alkyl group having from 1 to 6 carbon atoms. $R^2$ and $R^3$ each independently represents a hydrogen atom or an alkyl group having from 1 to 3 carbon atoms. $R^5$ and $R^6$ each independently represents an alkyl group having from 1 to 4 carbon atoms.).

7 Claims, 2 Drawing Sheets

[FIG. 1]
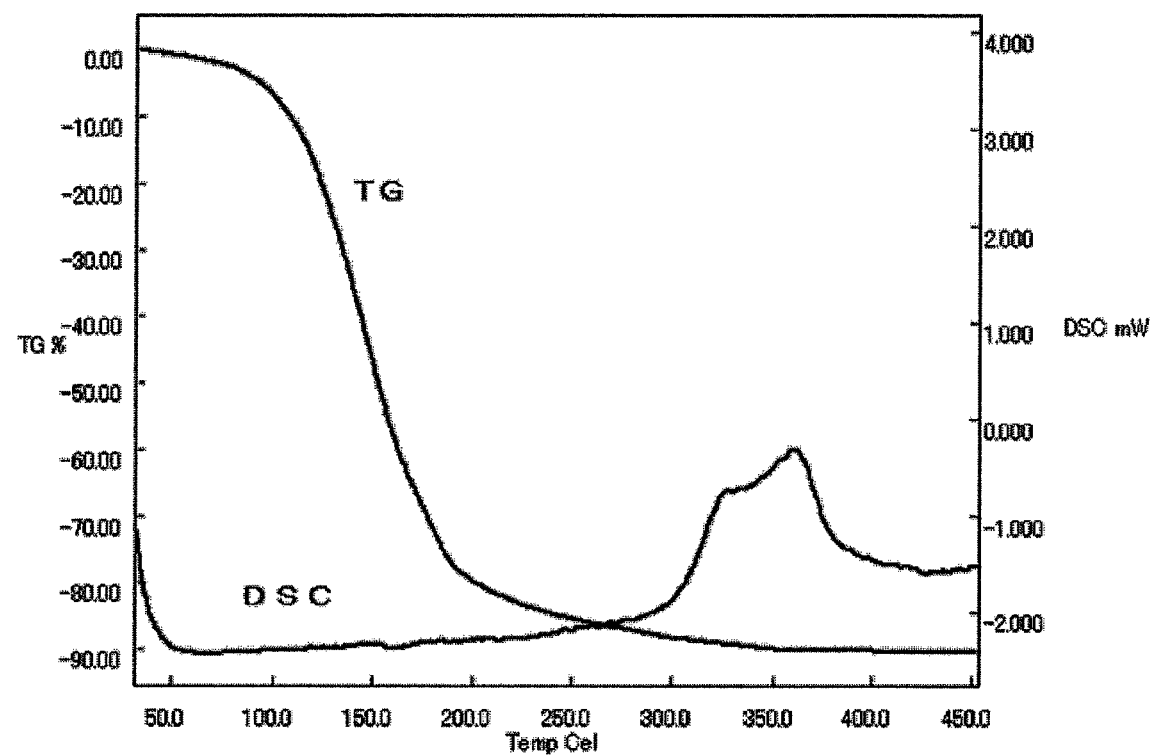

[FIG. 2]
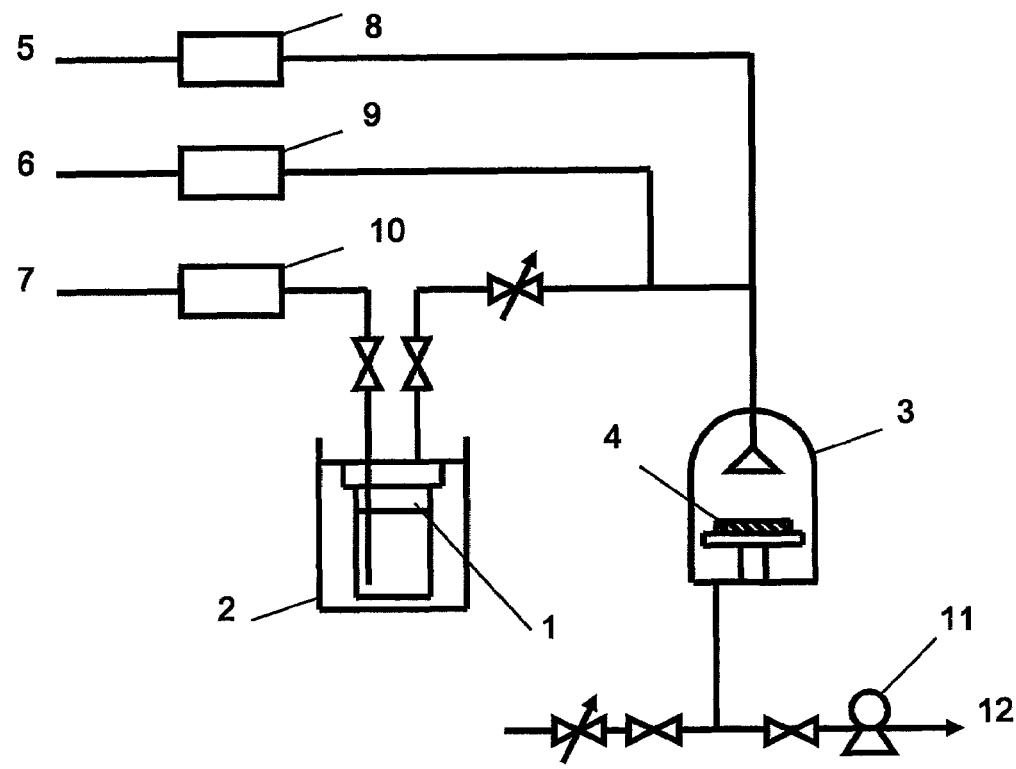
[FIG. 3]
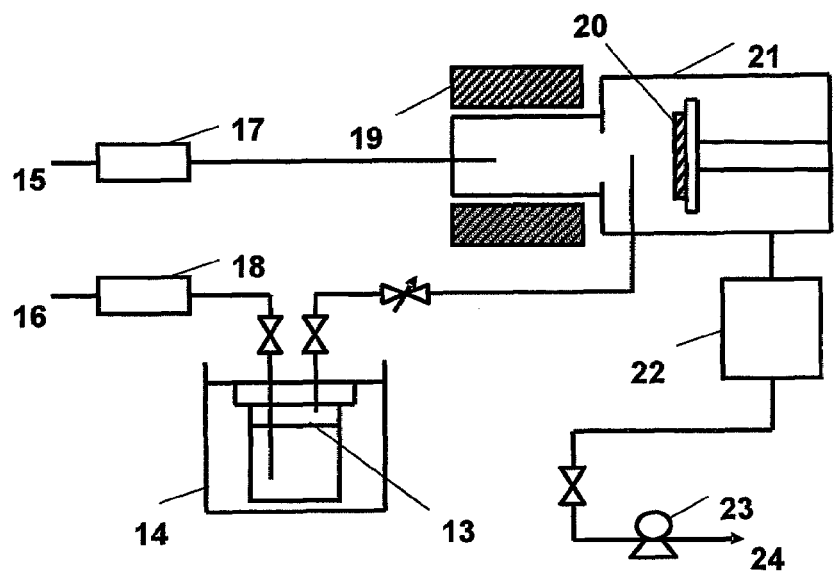

TITANIUM COMPLEXES, THEIR PRODUCTION METHODS, TITANIUM-CONTAINING THIN FILMS, AND THEIR FORMATION METHODS

TECHNICAL FIELD

The present invention relates to titanium complexes useful as raw materials for the production of a semiconductor element, their production methods, titanium-containing thin films, and their formation methods.

BACKGROUND ART

In the current production of a semiconductor element, a physical vapor deposition method (PVD method) by sputtering is mainly used in a method for forming a thin film of a wiring barrier, a capacitor dielectric and an electrode. However, in a semiconductor production in the next generation or later, it is required to form a uniform and thin film on a surface having a complicated three-dimensional structure of a miniaturized element. Therefore, the PVD method which is difficult to form a uniform film on a surface having concave and convex is not suitable. For this reason, a thin film formation method by CVD method which decomposes a raw material gas to deposit a film, or an atomic layer deposition method (ALD method) which decomposes a raw material adsorbed on a substrate surface to deposit a film is recently investigated.

Raw materials having appropriate vapor pressure and thermal stability and capable of vaporizing in a stabilized supply amount are selected in production raw materials for forming a thin film by CVD method or ALD method. Furthermore, it is one of necessary conditions that a film can be formed with a uniform film thickness on a surface having a complicated three-dimensional structure. Additionally, to stably vaporize in a constant supply amount, a liquid is preferred.

Titanium, titanium nitride and silicon-containing titanium nitride are nominated as materials of a barrier film of a semiconductor element and an electrode film of a capacitor in the next generation or later. Furthermore, titanium oxide and titanium-containing oxide are nominated as materials of a capacitor dielectric film.

Tetrakisamide complex $Ti(NRR')_4$ (R and R' are a methyl group or an ethyl group) and the like have hitherto been investigated as a raw material that forms a thin film of titanium, titanium nitride and silicon-containing titanium nitride by CVD method and ALD method (for example, see Patent Document 1). However, it is known that $Ti(NRR')_4$ has extremely high reactivity to water and reacts with a slight amount of water contained in a carrier gas, a reaction gas or the like used in film formation, and that oxygen is liable to be incorporated in a film formed. For example, it is reported that 10 atm % or more of oxygen is contained in a titanium nitride film formed by a remote plasma ALD method using titanium tetrakis(dimethylamide) $Ti(NMe_2)_4$ as a raw material (for example, see Non-Patent Document 1). A film containing oxygen has high specific resistance value, and therefore, does not satisfy the demand characteristics of a barrier layer. In other words, those tetrakisamide complexes are not preferred as a raw material for barrier layer formation.

On the other hand, tetraisopropoxotitanium $Ti(O^iPr)_4$, (diisopropoxo)(bis(2,2,6,6-tetramethylheptanedionato))-titanium $Ti(O^iPr)_2(THD)_2$, tetrakis(2-methoxy-1-methyl-1-propoxo)titanium $Ti(MMP)_4$ and the like have been investigated as raw materials for forming a titanium oxide film and a titanium-containing oxide film by CVD method of ALD method.

Where it is attempted to form a film using $Ti(O^iPr)_4$ as a raw material, $Ti(O^iPr)_4$ is extremely unstable to water, and as a result, there is the possibility that contamination of a slight amount of water vapor into a piping in an apparatus forms fine powder of titanium oxide, thereby clogging a pipe. Furthermore, where $Ti(O^iPr)_4$ is blown to a substrate and decomposed thereon, an alcohol is generated, and the alcohol is decomposed into water and an alkene. The water reacts with undecomposed $Ti(O^iPr)_4$ to form a fine powder of titanium oxide, and the fine powder is adhered to a film formation chamber and an exhaust port, resulting in the decrease of productivity. For this reason, $Ti(O^iPr)_4$ is not preferred as a raw material for the formation of a thin film used in a semiconductor element (see Patent Document 2).

Where a film is formed using $Ti(O^iPr)_2(THD)_2$ or $Ti(MMP)_4$, particularly where a titanium-containing composite oxide film is formed by CVD method, volatilization properties and decomposition properties of those to other metal supply source raw materials greatly differ, and as a result, there was the problem that it is difficult to control a composition of a thin film in a preferred ratio, thereby decreasing productivity.

Non-Patent Document 1: Journal of The Electrochemical Society, Vol. 152, page G29 (2005)

Patent Document 1: JP-A-2006-93551

Patent Document 2: JP-A-2004-196618

DISCLOSURE OF THE INVENTION

Problems that the Invention is to Solve

Objects of the present invention are to provide a novel titanium complex that has good vaporization characteristics and an excellent thermal stability, and becomes a raw material for forming a titanium-containing thin film by methods such as CVD method or ALD method, its production method, a titanium-containing thin film formed using the same, and its formation method.

Means for Solving the Problems

As a result of extensive and intensive investigations in view of the above-described present situation, the present inventors have found that a titanium complex represented by the general formula (1) is an excellent compound that can solve the above-described problems, and have reached to complete the present invention.

That is, the present invention relates to a titanium complex represented by the general formula (1)

[Chem. 1]

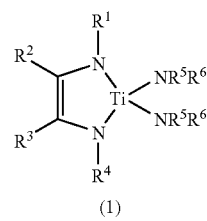

(1)

(In the formula, $R^1$ and $R^4$ each independently represents an alkyl group having from 1 to 6 carbon atoms which may be substituted with a fluorine atom. $R^2$ and $R^3$ each independently represents a hydrogen atom or an alkyl group having from 1 to 3 carbon atoms which may be substituted with a fluorine atom. $R^5$ and $R^6$ each independently represents an alkyl group having from 1 to 4 carbon atoms which may be substituted with a fluorine atom.)

The present invention further relates to a production method of the titanium complex represented by the general formula (1), which comprises reacting a diimine represented by the general formula (2)

[Chem. 2]

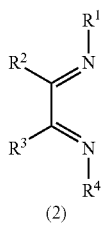

(2)

($R^1$ to $R^4$ are the same as defined above) and metallic lithium or a metallic sodium, and then reacting a tetrakisamide complex represented by the general formula (3)

[Chem. 3]

(3)

(In the formula, $R^5$ and $R^6$ are the same as defined above).

The present invention further relates to a formation method of a titanium-containing thin film, which comprises using the titanium complex (1) as a raw material.

The present invention further relates to a titanium-containing thin film formed by the method.

ADVANTAGE OF THE INVENTION

The titanium complex (1) of the present invention has good volatility characteristics and an excellent thermal stability, and can form a titanium-containing thin film by methods such as CVD method or ALD method.

BRIEF DESCRIPTION OF THE DRAWINGS

FIG. 1 is a view showing TG and DSC measurement results of Experimental Example 1.

FIG. 2 is a schematic view of CVD film formation apparatus used in Example 3.

FIG. 3 is a schematic view of PE-CVD film formation apparatus used in Examples 4 and 5.

DESCRIPTION OF REFERENCE NUMERALS AND SIGNS

1. Raw material vessel
2. Thermostatic bath
3. Reaction chamber
4. Substrate
5. Reaction gas
6. Diluent gas
7. Carrier gas
8. Mass flow controller
9. Mass flow controller
10. Mass flow controller
11. Vacuum pump
12. Exhaust
13. Raw material vessel
14. Thermostatic bath
15. Plasma source gas
16. Carrier gas
17. Mass flow controller
18. Mass flow controller
19. Plasma generation apparatus
20. Substrate
21. Reaction chamber
22. Oil diffusion pump
23. Oil rotational pump
24. Exhaust

BEST MODE FOR CARRYING OUT THE INVENTION

The present invention is described in more detail below.

The titanium complex of the present invention represented by the general formula (1) is capable of having a resonance structure represented by the following general formula (1a)

[Chem. 4]

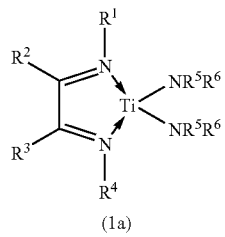

(1a)

(In the formula, $R^1$, $R^2$, $R^3$, $R^4$, $R^5$ and $R^6$ are the same as defined above), and is actually a resonance hybrid of a compound represented by the general formula (1) and a compound represented by the general formula (1a). In the present description, those compounds are combined and the combination is represented by the general formula (1) for simplicity.

In the present invention, examples of the alkyl group having from 1 to 6 carbon atoms represented by $R^1$ and $R^4$ include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group and a cyclobutylmethyl group.

Those alkyl groups may be substituted with a fluorine atom, and examples thereof include a trifluoromethyl group, a 2,2,2-trifluoroethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group.

Examples of the alkyl group having from 1 to 3 carbon atoms represented by $R^2$ and $R^3$ include a methyl group, an ethyl group, a propyl group, an isopropyl group and a cyclopropyl group. Those alkyl groups may be substituted with a fluorine atom, and examples thereof include a trifluoromethyl group, a 2,2,2-trifluoroethyl group, a perfluoroethyl group, a perfluoropropyl group and a perfluoroisopropyl group.

Examples of the alkyl group having from 1 to 4 carbon atoms represented by $R^5$ and $R^6$ include a methyl group, an ethyl group, a propyl group, an isopropyl group, a butyl group, an isobutyl group, a sec-butyl group and a tert-butyl group. Those alkyl groups may be substituted with a fluorine atom, and examples thereof include a trifluoromethyl group, a 2,2,2-trifluoroethyl group, a perfluoroethyl group, a perfluoropropyl group, a perfluoroisopropyl group, a perfluorobutyl group, a perfluoro-sec-butyl group and a perfluoro-tert-butyl group.

From the point that the titanium complex has good vapor pressure and excellent thermal stability, $R^1$ and $R^4$ in the titanium complex (1) are each independently preferably a secondary or tertiary alkyl group having from 3 to 6 carbon atoms. Specifically, an isopropyl group, a sec-butyl group, a tert-butyl group, a tert-pentyl group, a 1-methylbutyl group, 1,2-dimethylpropyl group, a 1-methylpentyl group, a 1,1-dimethylbutyl group, a 1,2-dimethylbutyl group, a 1,3-dimethylbutyl group, a 1-ethylbutyl group, a 1,1,2-trimethylpropyl group, 1,2,2-trimethylpropyl group, 1-ethyl-1-methylpropyl group, 1-ethyl-2-methylpropyl group, a cyclopropyl group, a cyclobutyl group, a cyclopentyl group and a cyclohexyl group, and a tert-butyl group is further preferred. $R^2$ and $R^3$ are preferably a hydrogen atom. $R^5$ and $R^6$ are each independently preferably a methyl group or an ethyl group, and a methyl group is further preferred.

The production method of the present invention is described below. It is known that when the diimine (2) and 2 equivalents or more of metallic lithium or metallic sodium are reacted in an organic solvent, a lithium-diimine complex or a sodium-diimine complex, represented by the general formula (4)

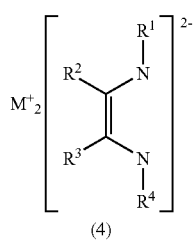

(4)

(In the formula, M represents a lithium atom or a sodium atom, and $R^1$, $R^2$, $R^3$ and $R^4$ are the same as defined above.) is formed (Organometallics, Vol. 17, page 4380 (1998)).

In reacting the tetrakisamide complex (3) with the lithium-diimine complex or sodium-diimine complex formed, reaction proceeds even though a solvent is not used. However, it is preferred to use a solvent in the point that the yield is good. For example, hydrocarbons such as pentane, hexane, heptane, octane, benzene, toluene, ethylbenzene and xylene; ethers such as diethyl ether, diisopropyl ether, glyme, dioxane and tetrahydrofuran; and the like can be used alone or mixtures thereof as a solvent. From the point that the yield is good, tetrahydrofuran, toluene, hexane or heptane is preferred, and toluene or hexane is particularly preferred.

In the point that the yield of the titanium complex (1) is good, it is preferred to react 2 equivalents or more of metallic lithium with the diimine (2), and then reacting the tetrakisamide complex (3).

The temperature in reacting the lithium-diimine complex or sodium-diimine complex with the tetrakisamide complex (3) is not limited. However, when the temperature is appropriately selected from a range of from 0 to 120° C., the titanium complex (1) can be obtained in good yield. The reaction time is not limited, but when the reaction time is appropriately selected from a range of from 1 minute to 120 hours, the reaction can be completed. To obtain the titanium complex (1) in good yield, it is preferred to react at a temperature in a range of from 30 to 110° C. for from 2 to 24 hours. When the lithium-diimine complex is used, it is further preferred to react at a temperature in a range of from 40 to 70° C. for from 2 to 12 hours. When the sodium-diimine complex is used, it is further preferred to react at a temperature in a range of from 50 to 80° C. for from 4 to 18 hours.

Collection and purification methods of the titanium complex (1) are not particularly limited, and the conventional methods can be used. For example, after completion of the reaction, insoluble matters by-produced are filtered to remove the same, the filtrate is concentrated under reduced pressure to obtain a crude product, and the crude product is distilled, sublimated or the like, thereby obtaining the titanium complex (1).

The diimine (2) as a raw material can be synthesized by reference to the conventional method (for example, Journal of the American Chemical Society, Vol. 120, page 12714, (1998)). The tetrakisamide complex (3) can be synthesized by reference to the conventional method (for example, Journal of the Chemical Society, page 3857, (1960)).

A titanium-containing thin film can be formed using the titanium complex (1) of the present invention as a raw material. For example, a titanium-containing thin film can be formed by CVD method or ALD method. In this case, the titanium complex (1) is vaporized and supplied onto a substrate. The vaporization method includes a method of placing the titanium complex (1) into a heated thermostatic bath, and blowing a carrier gas such as helium, neon, argon, krypton, xenon or nitrogen to vaporize the titanium complex (1), and a method of feeding the titanium complex (1) as it is or in a form of a solution to a carburetor, and heating the same to vaporize in the carburetor. Examples of the solvent used in the case of forming a solution include ethers such as 1,2-dimethoxyethane, diglyme, triglyme, dioxane, tetrahydro-furan and cyclopentylmethyl ether; and hydrocarbons such as hexane, cyclohexane, methyl cyclohexane, ethyl cyclohexane, heptane, octane, nonane, decane, benzene, toluene, ethylbenzene and xylene.

A film can be formed by decomposing the titanium complex (1) supplied as a gas onto a substrate. The decomposition can be performed by only heating, but plasma or light may be used in combination. Furthermore, the decomposition may be conducted by the co-presence of a reactive gas such as water, oxygen, ozone, hydrogen or ammonia.

The present invention is described in more detail by reference to the Examples, but the invention is not construed as being limited to those Examples.

EXAMPLE 1

Synthesis of Ti($^t$BuNC(H)C(H)N$^t$Bu)(NMe$_2$)$_2$

In an argon atmosphere, 212 mg (30.5 mmol) of lithium was added to a solution of 1.68 g (10.0 mmol) of N,N'-di(tert-butyl)-1,4-diaza-1,3-butadiene dissolved in 40 ml of tetrahydrofuran, followed by stirring at room temperature for 14 hours. The remaining lithium was filtered off, and a solvent was distilled away from a filtrate under reduced pressure. The remaining yellow solid was suspended in 10 ml of hexane, and a solution of 1.98 g (8.81 mmol) of titanium tetrakis (dimethylamide) dissolved in 20 ml of hexane was added thereto. After stirring at 50° C. for 4 hours, the resulting mixture was cooled to room temperature, and insoluble matters were filtered off. The solvent is distilled away under reduced pressure from the filtrate, and the residue obtained was distilled under reduced pressure to obtain 2.37 g of a deep red liquid (yield 88%).

$^1$H NMR (500 MHz, $C_6D_6$, δ/ppm) 5.86 (s, 2H), 3.06 (s, 12H), 1.28 (s, 18H) $^{13}$C NMR (125 MHz, $C_6D_6$, δ/ppm) 102.0, 58.7, 43.6, 31.6

EXPERIMENTAL EXAMPLE 1

Regarding the deep red liquid, the result of TG (thermogravimetric determination) measured at a temperature rising rate of 10° C./min in an atmosphere flowing argon at 400 ml/min and the result of DSC (differential scanning calorimetry) measured at a temperature rising rate of 10° C./min in a closed vessel were shown in FIG. 1. It is seen from TG to have appropriate vaporization characteristics as a raw material of CVD method or ALD method, and it is apparent from DSC that thermal stability is good.

EXAMPLE 2

Synthesis of Ti($^t$BuNC(H)C(H)N$^t$Bu)(NMe$_2$)$_2$

In an argon atmosphere, 1.14 g (49.6 mmol) of sodium was added to a solution of 4.00 g (23.8 mmol) of N,N'-di(tert-butyl)-1,4-diaza-1,3-butadiene dissolved in 25 ml of tetrahydrofuran, followed by stirring at room temperature for 14 hours. The remaining sodium was filtered off, and a solvent was distilled away from a filtrate under reduced pressure. The remaining red solid was suspended in 10 ml of toluene, and a solution of 5.08 g (22.7 mmol) of titanium tetrakis(dimethylamide) dissolved in 20 ml of toluene was added thereto. After stirring at 80° C. for 6 hours, the resulting mixture was cooled to room temperature, and insoluble matters were filtered off. The solvent is distilled away under reduced pressure from the filtrate, and the residue obtained was distilled under reduced pressure to obtain 3.05 g of a deep red liquid (yield 42%). This liquid was dissolved in $C_6D_6$, and $^1$H NMR and $^{13}$C NMR spectra were measured. As a result, the same spectra as obtained in Example 1 were obtained.

EXAMPLE 3

Formation of Titanium-containing Thin Film Using Ti($^t$BuNC(H)C(H)N$^t$Bu)(NMe$_2$)$_2$ Using Ti($^t$BuNC(H)C(H)N$^t$Bu)(NMe$_2$)$_2$ as a raw material, a film was formed on a SiO$_2$/Si substrate under the conditions of a thermostatic bath (2) maintained at 40° C., a carrier gas (7) (Ar) flow rate of 30 sccm, a raw material pressure of 200 Torr, a diluent gas (6) (Ar) flow rate of 280 sccm, a reaction gas (5) (O$_2$) flow rate of 90 scam, a substrate (4) temperature of 400° C. and a pressure in a reaction chamber (3) of 4 Torr using the CVD film formation apparatus shown in FIG. 2 by CVD method over 1 hour. When the film prepared was measured with fluorescent X-ray, characteristic X-ray of titanium was detected, and it was confirmed that a titanium-containing thin film was deposited.

EXAMPLE 4

Formation of Titanium-containing Thin Film Using Ti($^t$BuNC(H)C(H)N$^t$Bu)(NMe$_2$)$_2$ Using Ti($^t$BuNC(H)C(H)N$^t$Bu)(NMe$_2$)$_2$ as a raw material, a film was formed on a Si substrate under the conditions of a thermostatic bath (14) maintained at 40° C., a carrier gas (16) (N$_2$) flow rate of 27 sccm, a raw material pressure of 50 Torr, a plasma source gas (15) (N$_2$) flow rate of 5 sccm, a substrate (20) temperature of 300° C. and a pressure in a reaction chamber (21) of 0.2 Pa using the apparatus shown in FIG. 3 by PE-CVD method over 5 hours. The plasma was generated under the conditions of a resonance magnetic flux density of 875 gauss, a microwave wavelength of 2.45 GHz and a microwave output of 600 W. When the film prepared was measured with fluorescent X-ray, characteristic X-ray of titanium was detected. Furthermore, when the film composition was confirmed by X-ray photoelectron spectroscopy, it was found to be a thin film containing titanium and nitrogen. When the thin film was measured with a four probe resistance measuring instrument, conductivity was confirmed. When the film thickness was confirmed with SEM, it was found to be 10 nm.

EXAMPLE 5

Formation of Titanium-containing Thin Film Using Ti($^t$BuNC(H)C(H)N$^t$Bu)(NMe$_2$)$_2$ Using Ti($^t$BuNC(H)C(H)N$^t$Bu)(NMe$_2$)$_2$ as a raw material, a film was formed on a Si substrate under the conditions of a thermostatic bath (14) maintained at 40° C., a carrier gas (16) (Ar) flow rate of 41 sccm, a raw material pressure of 50 Torr, a plasma source gas (15) (Ar) flow rate of 10 sccm, a substrate (20) temperature of 300° C. and a pressure in a reaction chamber (21) of 0.2 Pa using the apparatus shown in FIG. 3 by PE-CVD method over 5 hours. The plasma was generated under the conditions of a resonance magnetic flux density of 875 gauss, a microwave wavelength of 2.45 GHz and a microwave output of 600 W. When the film prepared was measured with fluorescent X-ray, characteristic X-ray of titanium was detected. Furthermore, when the film composition was confirmed by X-ray photoelectron spectroscopy, it was found to be a thin film containing titanium and nitrogen. When the thin film was measured with a four probe resistance measuring instrument, conductivity was confirmed. When the film thickness was confirmed with SEM, it was found to be 40 nm.

While the invention has been described in detail and with reference to specific embodiments thereof, it will be apparent to one skilled in the art that various changes and modifications can be made therein without departing from the spirit and scope thereof.

This application is based on Japanese patent application (Patent Application No. 2005-326885) filed Nov. 11, 2005 and Japanese patent application (Patent Application No. 2006-242617) filed Sep. 7, 2006, the entire contents thereof being hereby incorporated by reference.

INDUSTRIAL APPLICABILITY

The titanium complex (1) of the present invention has good vaporization characteristics and an excellent thermal stability, and can form a titanium-containing thin film by methods such as CVD method or ALD method. The industrial value of the present invention is remarkable.

The invention claimed is:

1. A titanium complex represented by the general formula (1)

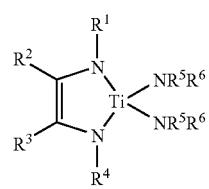

(1)

wherein $R^1$ and $R^4$ each independently represents an alkyl group having from 1 to 6 carbon atoms which may be substituted with a fluorine atom, $R^2$ and $R^3$ each independently represents a hydrogen atom or an alkyl group having from 1 to 3 carbon atoms which may be substituted with a fluorine atom, and $R^5$ and $R^6$ each independently represents an alkyl group having from 1 to 4 carbon atoms which may be substituted with a fluorine atom.

2. The titanium complex as claimed in claim 1, wherein $R^1$ and $R^4$ each independently represents a secondary or tertiary alkyl group having from 3 to 6 carbon atoms, $R^2$ and $R^3$ represent a hydrogen atom, and $R^5$ and $R^6$ each independently represents a methyl group or an ethyl group.

3. The titanium complex as claimed in claim 1, wherein $R^1$ and $R^4$ represent a tert-butyl group, $R^2$ and $R^3$ represent a hydrogen atom, and $R^5$ and $R^6$ represent a methyl group.

4. A production method of a titanium complex represented by the general formula (1):

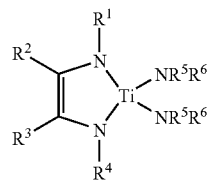

(1)

wherein $R^1$ and $R^4$ each independently represents an alkyl group having from 1 to 6 carbon atoms which may be substituted with a fluorine atom, $R^2$ and $R^3$ each independently represents a hydrogen atom or an alkyl group having from 1 to 3 carbon atoms which may be substituted with a fluorine atom, and $R^5$ and $R^6$ each independently represents an alkyl group having from 1 to 4 carbon atoms which may be substituted with a fluorine atom, which comprises reacting a diimine represented by the general formula (2):

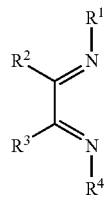

(2)

wherein $R^1$, $R^2$, $R^3$ and $R^4$ are the same as defined above, and metallic lithium or metallic sodium, and then reacting a tetrakisamide complex represented by the general formula (3):

$$Ti(NR^5R^6)_4 \qquad (3)$$

wherein $R^5$ and $R^6$ are the same as defined above.

5. The production method as claimed in claim 4, wherein $R^1$ and $R^4$ each independently represents a secondary or tertiary alkyl group having from 3 to 6 carbon atoms, $R^2$ and $R^3$ represent a hydrogen atom, and $R^5$ and $R^6$ each independently represents a methyl group or an ethyl group.

6. The production method as claimed in claim 4, wherein $R^1$ and $R^4$ represent a tert-butyl group, $R^2$ and $R^3$ represent a hydrogen atom, and $R^5$ and $R^6$ represent a methyl group.

7. A method of forming a titanium-containing thin film, where the titanium complex as claimed in claim 1 is deposited on a substrate in the form of a thin film containing titanium.

* * * * *